United States Patent [19]

Ernst et al.

[11] Patent Number: 5,082,783
[45] Date of Patent: Jan. 21, 1992

[54] ENHANCED SECRETION OF HETEROLOGOUS PROTEINS BY HOSTS USING SUBSTITUTED PROMOTERS

[75] Inventors: Joachim F. Ernst, Veyrier; Ursula Schmeissner, Geneva, both of Switzerland

[73] Assignee: Biogen, Inc., Cambridge, Mass.

[21] Appl. No.: 452,632

[22] Filed: Dec. 18, 1989

Related U.S. Application Data

[63] Continuation of Ser. No. 827,432, Feb. 10, 1986, abandoned.

[30] Foreign Application Priority Data

Nov. 25, 1985 [GB] United Kingdom ............... 8529014

[51] Int. Cl.$^5$ ................... C07H 15/12; C12P 21/00; C12N 1/16
[52] U.S. Cl. ................... 435/69.1; 435/61.4; 435/69.5; 435/69.8; 435/69.9; 435/212; 435/219; 435/69.3; 536/27; 935/48; 935/37; 935/47
[58] Field of Search ............ 435/69.1, 69.2, 69.3, 435/69.4, 69.5, 69.9, 69.6, 69.8, 172.3, 255, 212, 256, 219, 254, 320, 252.3, 252.33; 935/47, 48, 37; 536/27

[56] References Cited

U.S. PATENT DOCUMENTS

| | | | |
|---|---|---|---|
| 4,338,397 | 7/1982 | Gilbert et al. | 435/69.1 |
| 4,411,994 | 10/1983 | Gilbert et al. | 435/172.3 X |
| 4,546,082 | 10/1985 | Kurjan et al. | 435/172.3 |
| 4,588,684 | 5/1986 | Brake | 435/69.1 |

FOREIGN PATENT DOCUMENTS

| | | | |
|---|---|---|---|
| 0123228 | 10/1984 | European Pat. Off. | 435/69.1 |
| 0128733 | 12/1984 | European Pat. Off. | 435/69.1 |

OTHER PUBLICATIONS

L. Bennetzen and B. D. Hall, "Codon Selection In Yeast", *J. Biol. Chem.*, 257, pp. 3026-3031 (1982).
J. D. Beggs, "Multiple-Copy Yeast Vectors", *Molecular Genetics In Yeast*, Alfred Benzon Symposium, 16, pp. 383-395 (1981).
G. A. Bitter et al., "Secretion Of Foreign Proteins From *Saccharomyces cerevisiae* . . . ", *Proc. Natl. Acad. Sci. USA*, 81, pp. 5330-5334 (1984).
D. Botstein et al., "Sterile Host Yeasts (SHY): A Eukaryotic System Of Biological Containment For Recombinant DNA Experiments", *Gene*, 8, pp. 17-24 (1979).
A. Brake et al., "α-Factor-Directed Synthesis And Secretion Of Mature Foreign Proteins In *Saccharomyces cerevisiae*", *Proc. Natl. Acad. Sci. USA*, 81, pp. 4642-4646 (1984).
G. Buell et al., "Optimizing The Expression In *E. coli* Of A Synthetic Gene Encoding Somatomedin-C (IG-F-I)", *Nucl. Acids Res.*, 13, pp. 1923-1939 (1985).
C. N. Chang et al., "Recognition And Cleavage Of Hybrid Invertase Signals . . . ", *The Molecular Biology of Yeast*, Cold Spring Harbor Laboratory, p. 393 (1983).
Chao et al., "Effect of the Bacterial Growth Rate on Replication Control of Plasmid pBR322 in *Escherichia coli*", *Mol. Gen. Genet.*, 203, pp. 143-149 (1986).
D. DiMaio et al., "Bovine Papillomavirus Vector That Propagates As A Plasmid In Both Mouse And Bacterial Cells", *Proc. Natl. Acad. Sci. USA*, 79, pp. 4030-4034 (1982).

(List continued on next page.)

*Primary Examiner*—Robin L. Teskin
*Attorney, Agent, or Firm*—James F. Haley, Jr; Margaret A. Pierri; Leon R. Yankwich

[57] ABSTRACT

Improved secretion of heterologous proteins by hosts such as yeast by using promoters of at most intermediate strength with heterologous DNA secretion signal sequences is disclosed. A promoter of at most intermediate strength, such as the actin (ACT) or iso-1-cytochrome c (CYC1) promoter in *S. cerevisiae* is operatively linked to a DNA signal sequence, such as the Mfα1 signal sequence. A DNA sequence for a selected protein, such as somatomedin C (SMC), tissue plasminogen activator (TPA) or tumor necrosis factor (TNF), may be operatively linked to the DNA signal sequence.

14 Claims, 11 Drawing Sheets

OTHER PUBLICATIONS

M. J. Dobson et al., "Expression In *Saccharomyces cerevisiae* Of Human Interferon-Alpha Directed By The TRP1 5' Region", *Nucl. Acids Res.*, 11, pp. 2287-2302 (1983).

S. D. Emr, "An MF 1-SUC2 (α-Factor-Invertase) Gene Fusion For Study Of Protein Localization And Gene Expression In Yeast", *Proc. Natl. Acad. Sci. USA*, 80, pp. 7080-7084 (1983).

E. Erhart and C. P. Hollenberg, "The Presence Of A Defective LEU2 Gene On 2μ DNA Recombinant Plasmids . . . ", *J. Bacteriol.*, 156, pp. 625-635 (1983).

J. F. Ernst and R. C. Chan, "Characterization Of *Saccharomyces cerevisiae* . . . ", *J. Bacteriol.*, 163, pp. 8-14 (1985).

D. Gallwitz and I. Sures, "Structure Of A Split Yeast Gene: Complete Nucleotide Sequence Of The Actin Gene . . . ", *Proc. Natl. Acad. Sci. USA*, 77, pp. 2546-2550 (1980).

D. Gallwitz et al., "The Actin In Yeast *Saccharomyces cerevisiae*: 5' and 3' End Mapping . . . ", *Nucl. Acids Research*, 9, pp. 6339-6351 (1981).

A. Haselbeck and W. Tanner, "O-Glycosylation In *Saccharomyces cerevisiae* Is Initiated At The Endoplasmic Reticulum", *FEBS Letters*, 158, pp. 335-338 (1983).

H. J. Himmelfarb et al., "Isolation Of The SUP45 Omnipotent Suppressor Gene Of *Saccharomyces cerevisiae* . . . ", *Mol. Cell. Biol.*, 5, pp. 816-822 (1985).

R. A. Hitzeman et al., "Isolation And Characterization Of The Yeast 3-Phosphoglycerokinase Gene . . . ", *J. Biol. Chem.*, 255, pp. 12073-12080 (1980).

C. P. Hollenberg, "Cloning With 2 m DNA Vectors And The Expression Of Foreign Genes In *Saccharomyces cerevisiae*", *Curr. Top Microbiol. Immunol.*, pp. 119-144 (1982).

D. Julius et al., "Isolation Of The Putative Structural Gene For The Lysine-Arginine-Cleaving Endopeptidase . . . ", *Cell*, 37, pp. 1075-1089 (1984).

D. Julius et al., "Glycosylation And Processing Of Prepro-α-Factor Through The Yeast Secretory Pathway", *Cell*, 36, pp. 309-318 (1984).

C. H. Kim and J. R. Warner, "Messenger RNA For Ribosomal Proteins In Yeast", *J. Molec. Biol.*, 165, pp. 78-89 (1983).

J. Kurjan, "α-Factor Structural Gene Mutations In *Saccharomyces cerevisiae*: Effects On α-Factor Production And Mating", *Mol. Cell. Biol.*, 5, pp. 787-796 (1985).

J. Kurjan and I. Hershkowitz, "Structure Of A Yeast Pheromone Gene (MF): A Putative α-Factor Precursor . . . ", *Cell*, 30, pp. 933-943 (1982).

U. K. Laemmli, "Cleavage Of The Structural Proteins During The Assembly Of The Head Of Bacteriophage T4", *Nature*, 227, pp. 680-685 (1970).

J. Mellor et al., "Factors Affecting Heterologous Gene Expression In *Saccharomyces cerervisi*", *Gene*, 33, pp. 215-226 (1985).

B. Meyhack et al., "High Levels Of Expression Of Foreign Genes Under The Control . . . ", *The Molecular Biology of Yeast*, Cold Spring Harbor Laboratory, p. 156 (1983).

K. A. Nasmyth and S. I. Reed, "Isolation Of Genes By Complementation In Yeast . . . ", *Proc. Natl. Acad. Sci. USA*, 77, 2119-23 (1980).

A. Oka et al., "Nucleotide Sequence Of The Kanamycin Resistance Transposon Tn903", *J. Molec. Biol.* 147, pp. 217-226 (1981).

B. A. Oostra et al., "Transforming Acitivity Of Polyoma Virus Middle-T Antigen Probed By Site-Directed Mutagenesis", *Nature*, 304, pp. 456-459 (1983).

D. Pennica et al., "Cloning And Expression Of Human Tissue-Type Plasminogen Activator cDNA In *E. coli*", *Nature*, 301, pp. 214-221 (1983).

D. Pennica et al., "Human Tumour Necrosis Factor: Precursor Structure, Expression And Homology To Lymphotoxin", *Nature*, 312, pp. 724-729 (1984).

A. Granelli-Piperno and E. Reich, "A Study Of Proteases And Protease-Inhibitor Complexes In Biological Fluids", *J. Exp. Med.*, 148, pp. 223-234 (1978).

J. A. Rothblatt and D. I. Meyer, "Secretion In Yeast: Reconstitution Of The Translocation And Glycosylation . . . ", *Cell*, 44, pp. 619-628 (1986).

Rymond et al., "The Expression in Yeast of the *Escherichia coli* galK Gene on CYC1::galK Fusion Plasmids", *Gene*, 25, pp. 249-262 (1983).

OTHER PUBLICATIONS

T. J. Silhavy et al., "Mechanisms Of Protein Localization", *Microbiol. Rev.*, 47, pp. 313-334 (1983).

A. Singh et al., "*Saccharomyces cerevisiae* Contains Two Discrete Genes Coating For the α-Factor Pheromone", *Nucl. Acids. Res.*, 11, pp. 4049-4063 (1983).

A. Singh et al., "Synthesis, Secretion And Processing Of α-Factor-Interferon Fusion Proteins In Yeast", *Nucl. Acids. Res.*, 12, pp. 8927-8938 (1984).

Steuber et al., "Transcription From Efficient Promoters Can Interfere with Plasmids Replication and Diminish Expression . . . ", *EMBO*, vol. 1, No. 11, pp. 1399-1909 (1982).

Villa-Komaroff et al., "A Bacterial Clone Synthesizing Proinsulin", *Proc. Natl. Acad. Sci. USA*, 75, pp. 3727-3731 (1978).

K. S. Zaret and F. Sherman, "DNA Sequence Required For Efficient Transcription Termination In Yeast", *Cell*, 28, pp. 563-573 (1982).

R. S. Zitomer and B. D. Hall, "Yeast Cytochrome c Messenger RNA", *J. Biol. Chem.*, 251, pp. 6320-6326 (1976).

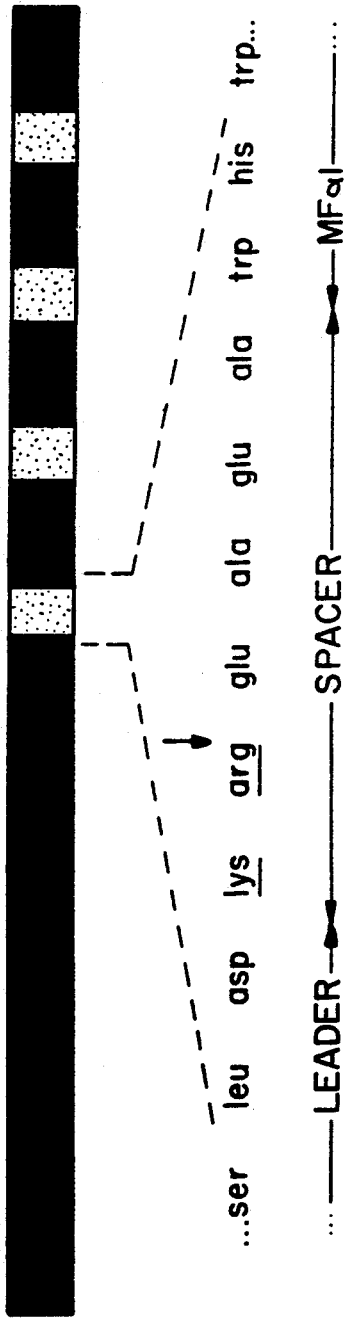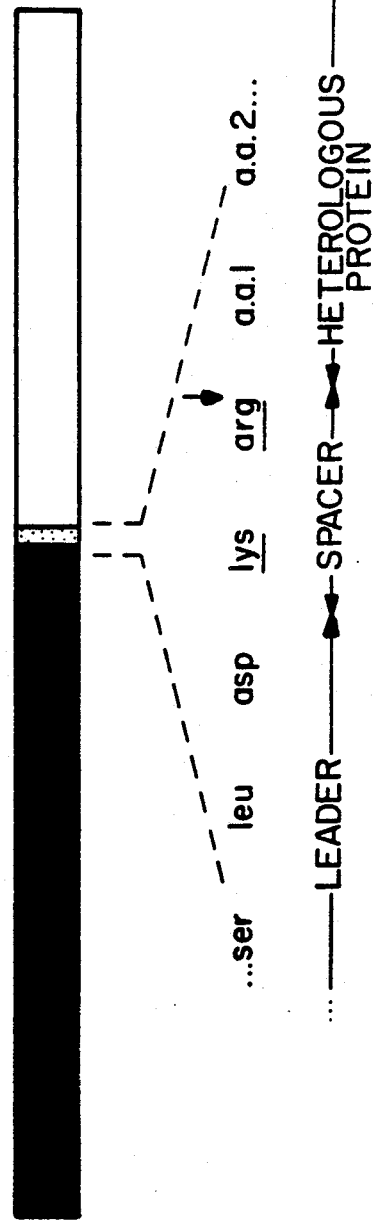
FIG. 1A
FIG. 1B

1. DIGEST WITH XhoI
2. TREAT WITH Bal31
3. DIGEST WITH EcoRI
4. FILL-IN WITH dNTPs
5. RELIGATE

```
            -20        -10        +1
ACTIN   GATCGAAAATTTACTGAATTAACAATGGATTCTGG
pEX-5   GAATTC
pEX-7   GATCGAAAATTTACTGAATTC
pEX-8   GATCGAAAATTTACTGAATTAACAATGGATTCTGAATTC
```

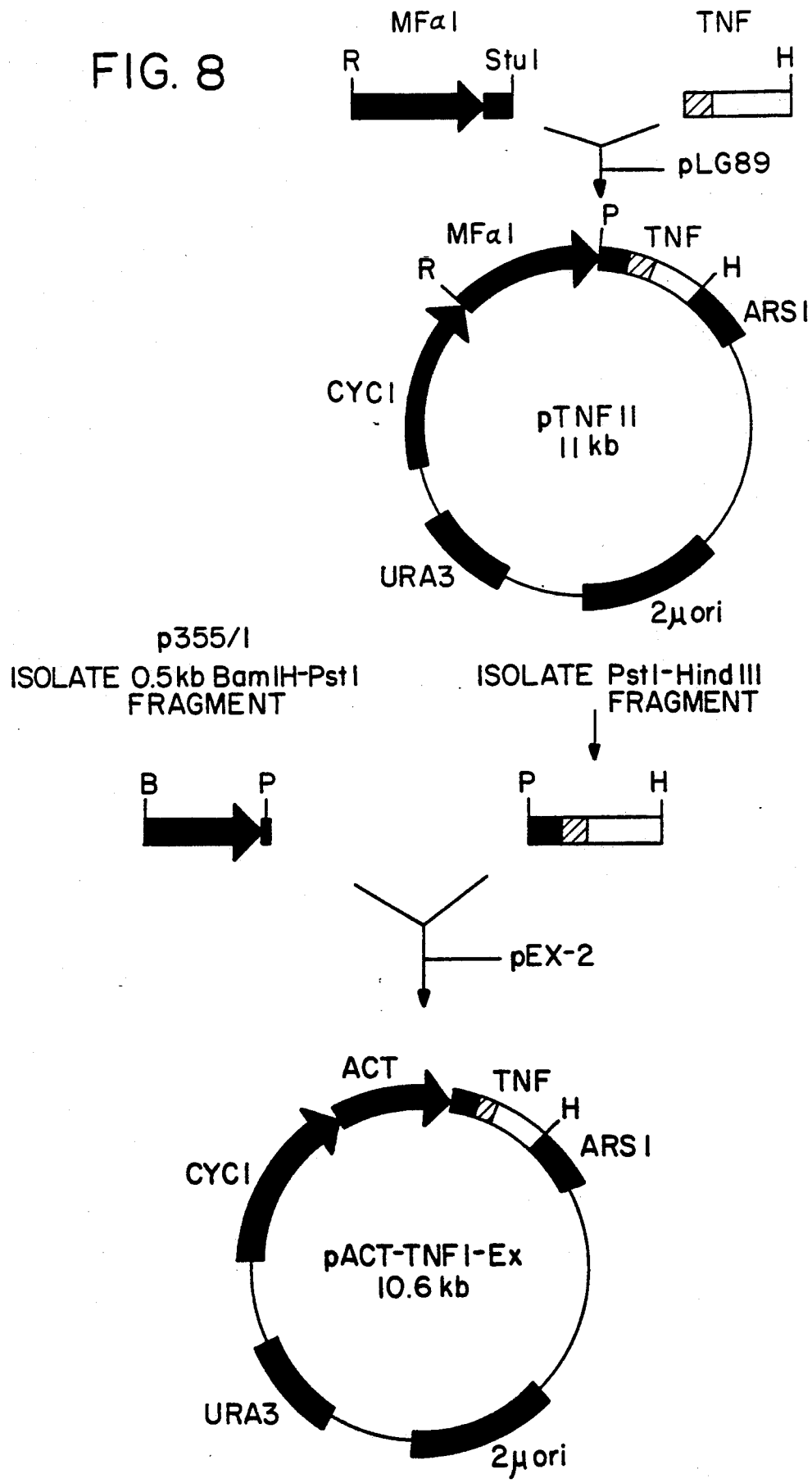

ENHANCED SECRETION OF HETEROLOGOUS PROTEINS BY HOSTS USING SUBSTITUTED PROMOTERS

This is a continuation of application Ser. No. 06/827,432, filed Feb. 10, 1986, entitled Enhanced Secretion of Heterologous Proteins By Hosts Using Substituted Promoters now abandoned.

TECHNICAL FIELD OF THE INVENTION

This invention relates to expression systems and recombinant DNA molecules that facilitate enhanced secretion of heterologous proteins by hosts, to hosts comprising such recombinant DNA molecules and to methods of producing desired proteins using such hosts.

BACKGROUND OF THE INVENTION

Proteins prepared by recombinant DNA methods are sometimes difficult to isolate because the protein must be extracted from the transformed microorganism by means such as cell lysis that typically destroy the microorganism. Obtaining sufficiently pure protein in high yield from such extraction procedures is difficult because of the large number of different organic compounds liberated when lysis takes place.

One attractive alternative to typical separation procedures is to have the host secrete the selected protein into its environment. A secreted protein is more easily separated from the culture medium, and the microorganism can survive the separation process to produce and to secrete more of the desired protein.

Most proteins naturally secreted by prokaryotes and eukaryotes are initially synthesized in the form of precursors containing an amino-terminal extension several amino acids long. This extension, called a secretion leader or signal sequence, allows the precursor protein to cross the cell membrane of the microorganism and enter the culture medium or periplasmic space of the cell. During secretion, the secretion leader is cleaved from the protein, leading to the presence of mature protein in the culture medium or periplasmic space.

Although the rate of secretion in bacteria is typically very low, bacterial secretion has been used with recombinant DNA technology. See, for example, U.S. Pat. Nos. 4,411,994 and 4,338,397, and Villa-Komaroff et al., *Proc. Natl. Acad. Sci. USA*, 75, 3727-31 (1978).

The general safety of yeasts and human experience with yeast fermentation have made yeasts desirable candidates for use as hosts in recombinant DNA technology. However, reported attempts to obtain secreted mature proteins from recombinant yeasts have suffered from low yields. See, for example, C. N. Chang et al., "Recognition and Cleavage of Hybrid Invertase Signals and Mature Forms of Human Interferon (IFN-α2) in Yeast," Meeting Abstracts, *The Molecular Biology of Yeast*, Cold Spring Harbor Laboratory, Cold Spring Harbor, N.Y., p. 393 (1983); B. Meyhack and A. Hinnen, "High Levels of Expression of Foreign Genes Under the Control of the Yeast PH05 Promoter," Meeting Abstracts, *The Molecular Biology of Yeast*, Cold Spring Harbor Laboratory, Cold Spring Harbor, N.Y., p. 156 (1983); S. D. Emr, "An MFα1-SUC2 (α-Factor-Invertase) Gene Fusion for Study of Protein Localization and Gene Expression in Yeast," *Proc. Natl. Acad. Sci. USA*, 80, pp. 7080-84 (1983); A. Brake et al., "α-Factor-Directed Synthesis and Secretion of Mature Foreign Proteins in *Saccharomyces cerevisiae*," *Proc. Natl. Acad. Sci. USA,* 81, pp. 4642-46 (1984); G. A. Bitter et al., "Secretion of Foreign Proteins from *Saccharomyces cerevisiae* Directed by α-Factor Gene Fusions," *Proc. Natl. Acad. Sci. USA*, 81, pp. 5330-34 (1984); A. Singh et al., "Synthesis, Secretion and Processing of α-Factor-Interferon Fusion Proteins in Yeast," *Nucl. Ac. Res.*, 12, pp. 8927-38 (1984); European Patent Application 123,228; and European Patent Application 128,733; and G. Bitter et al, "Secretion of Foreign Proteins from *Saccharomyces cerevisiae* Directed by α-Factor Pheromone," *Nucl. Ac. Res.*, 11, pp. 4049-63 (1983).

SUMMARY OF THE INVENTION

The present invention solves the foregoing problems by providing expression systems that facilitate enhanced secretion of heterologous proteins. We have found that using a promoter of at most intermediate strength and a heterologous DNA secretion signal sequence in a multicopy vector results in a higher yield of a desired protein from the host compared to hosts transformed by a multicopy vector using a strong promoter.

Thus, one embodiment of the present invention comprises a DNA sequence that is an expression and secretion control sequence for producing and secreting a selected protein from a host in which the protein is made, said sequence comprising (a) a promoter that is active in said host and is of at most intermediate strength, and (b) a heterologous DNA secretion signal sequence, recognized by said host, beginning with a start codon, operatively linked to said promoter. The expression and secretion control sequence may then be operatively linked to a DNA sequence coding for a desired protein and employed to transform a host to produce and secrete the desired protein. Yeast is a preferred host, and the actin (ACT) and iso-1-cytochrome c (CYC1) promoters are preferred promoters for yeast hosts. *S. cerevisiae* is the most preferred host. When the host is *S. cerevisiae,* the secretion signal sequence is preferably the secretion signal sequence of the MFα1 gene.

The present invention also relates to hosts transformed by the recombinant DNA molecules discussed above and to methods of using transformed hosts in the preparation and secretion of desired proteins.

BRIEF DESCRIPTION OF THE DRAWINGS

FIG. 1A shows the structure of the MFα1 secretion precursor. Stippled regions indicate spacer regions separating the MFα1 repeats. During secretion the secretion leader is cleaved off at the position indicated by the arrow.

FIG. 1B shows a general scheme for the construction of a yeast secretion precursor comprising the alpha mating factor (MFα1) secretion leader fused to the desired heterologous protein. During secretion, the secretion leader is cleaved at the position indicated by the arrow.

FIG. 3B shows growth (as reflected by optical density at 600 nm) and FIG. 3A shows SMC levels in the culture fluid of yeast strain BJ1991 transformed with URA3-type expression vectors. The CYC1 promoter construction (p336/1) is shown by (●); the ACT promoter construction (p364/1) by (▲); and the MFαl promoter construction (p446/1) by (■).

FIG. 7B shows growth (as reflected by optical density at 600 nm) and FIG. 7A shows SMC levels in the culture fluid of yeast strain BJ1991 transformed with LEU2-type expression vectors. The CYC1 promoter construction (504/1) is shown by (●); the ACT promoter construction (p482/18) by (▲); and the MFαl promoter construction (pMF-SMC, rearranged) by (■).

FIG. 8 shows the construction of secretion vectors for TNF.

DETAILED DESCRIPTION OF THE INVENTION

Figure 2:
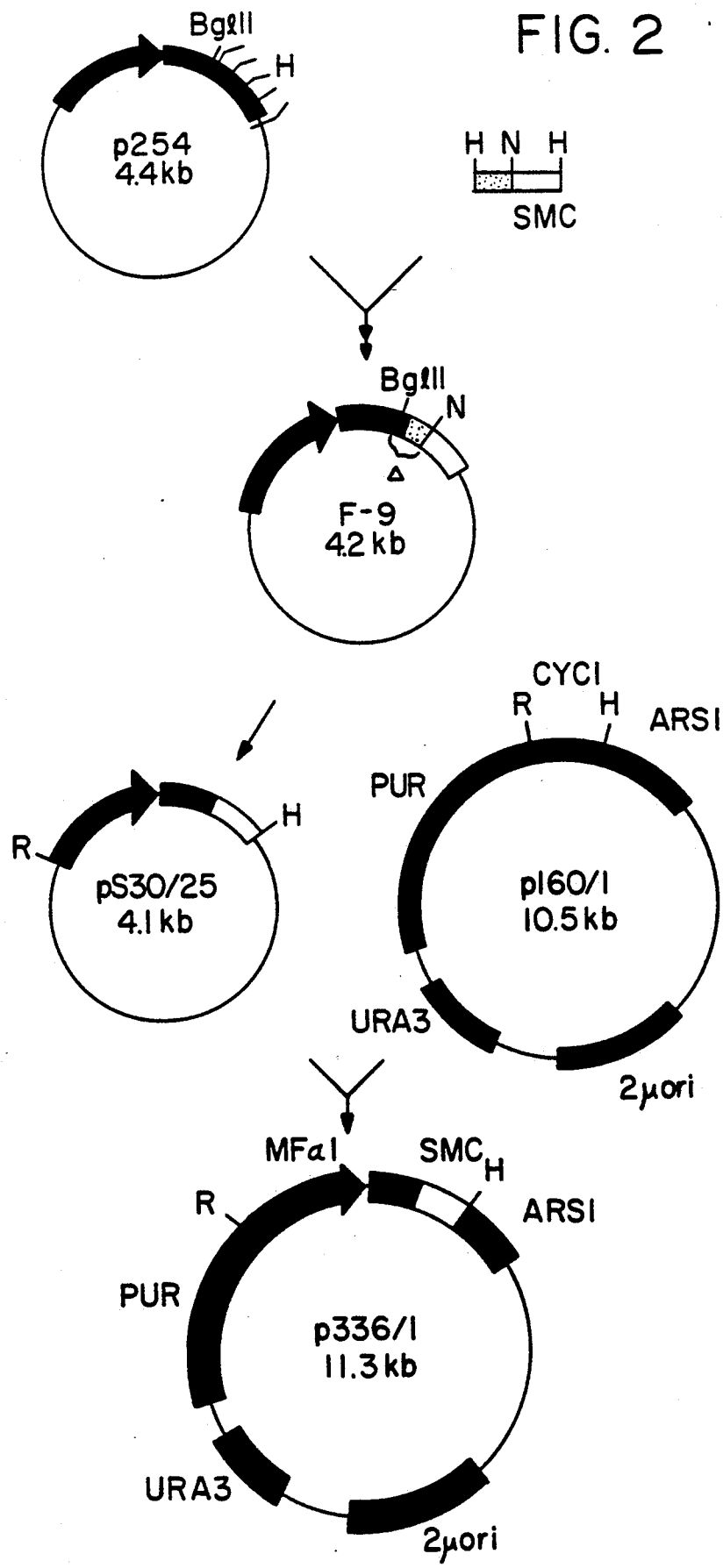
FIG. 2 shows the construction of a gene fusion between the MFα1 expression control sequence and the SMC gene and insertion of the MFα1/SMC fusion into a yeast expression vector.

In order that the invention may be more fully understood, the following detailed description is provided. In this specification, some of the following terms are used:

Cloning—the process of obtaining a population of organisms or DNA sequences derived from one such organism or sequence by asexual reproduction.

Recombinant DNA Molecule or Hybrid DNA—A molecule consisting of sequences of DNA from different genomes which have been joined end-to-end outside of living cells and that can be maintained in living cells.

Protein—A polypeptide containing a linear series of more than fifty amino acids, e.g., proinsulin, serum albumin, human growth hormone, parathyroid hormone, and interferon. As used herein, however, a protein also comprises a polypeptide chain of fewer than fifty amino acids.

Polypeptide—A linear series of amino acids connected one to the other by peptide bonds between the amino and carboxy groups of adjacent amino acids.

Expression—The process undergone by a gene to produce a polypeptide or protein. It is a combination of transcription and translation.

Transcription—The process of producing mRNA from a gene.

Translation—The process of producing a protein or polypeptide from mRNA.

Promoter—The region of DNA responsible for binding RNA polymerase to initiate transcription. In bacterial expression systems a promoter is located before the ribosome binding site. A strong promoter is defined as one that has a strong affinity for RNA polymerase and that would accordingly be expected to aid in obtaining high expression rates. A promoter of intermediate strength has a lower affinity for RNA polymerase.

In recombinant systems, the strength of a promoter may be affected by the host, the desired protein and the expression vector of the recombinant system. The effects of these factors are more fully discussed below. In systems that do not secrete the desired protein, i.e., intracellular expression systems, levels of mRNA and levels of expressed protein are proportional to promoter strength. In intracellular expression systems, no changes of plasmid copy number have been observed with variation of promoter strength. J. Mellor et al, "Factors Affecting Heterologous Gene Expression in Saccharomyces cerevisiae," Gene, 33, pp. 215-26 (1985). In secretion expression systems, we have discovered that promoter strength may affect the number of copies of a multicopy expression vector produced within a given host. In secretion expression systems, a host will produce many copies of a multicopy vector that contains an intermediate or weak promoter but will produce fewer copies of a multicopy vector that contains a strong promoter. An estimate of the strength of a promoter may be based on the percent of total mRNA in a cell produced by the expression control sequences of that promoter. Table 1 shows a list of genes, including their associated promoters and associated mRNA, as described in the literature. A characterization of the promoter strength is also included.

TABLE 1

| Gene | Protein | Percent of Total mRNA | Reference | Characterization of Promoter Strength |
|---|---|---|---|---|
| pgap 63 | G3PDH | 1.5-6 | 1 | very strong |
| peno 8 | enolase | 1-3 | 1 | very strong |
| ADH-I | alcoholdehydrogenase | 0.7-2 | 1 | very strong |
| | histone 2B | 0.4 | 1 | strong |
| tcm | ribosomal protein P1 | 0.3 | 2, 3 | strong |
| act | actin | 0.15 | 3 | intermediate |
| cyc1 | iso-1-cytochrome c | 0.05 | 1 | weak |
| URA3 | — | 0.008 | 2 | very weak |
| cyc7 | iso-2-cytochrome c | 0.003 | 1 | very weak |
| trp1 | — | <0.01 | 4 | very weak |

1. J. L. Bennetzen and B. D. Hall, "Codon Selection in Yeast," J. Biol. Chem., 257, pp. 3026-31 (1982).
2. C. H. Kim and J. R. Warner, "Messenger RNA for Ribosomal Proteins in Yeast," J. Mol. Biol., 165, pp. 78-89 (1983).
3. H. J. Himmelfarb et al., "Isolation of the SUP45 Omnipotent Suppressor Gene of Saccharomyces cerevisiae and Characterization of its Gene Product," Mol. Cell. Biol., 5, pp. 816-22 (1985).
4. M. J. Dobson et al., "Expression in Saccharomyces cerevisiae of Human Interferon-Alpha Directed by TRP1 5' Region," Nucl. Ac. Res., 11, pp. 2287-2302 (1983).

Generally, promoters of glycolytic genes are considered "strong." Those skilled in the art will understand, however, that promoters may not have the same strength within different strains of a host, with different desired proteins or in different multicopy vectors. In S. cerevisiae, for example, the MFαl promoter is active in MATα strains, but inactive in MATa strains. Those skilled in the art will appreciate that promoter strength depends upon many factors. Merely because a promoter is unacceptable with respect to one combination of host, vector and desired protein does not mean that the promoter will not be acceptable for another combination of host, vector and desired protein.

Promoters of the present invention should be selected so that the combination of promoter strength and copy number of the multicopy vector provides optimum yields of desired protein. Promoters of intermediate strength provide the best combination of promoter strength with high copy number. Weaker promoters, in combination with high copy numbers, are also within the scope of the invention. Strong promoters adversely affect the copy number of the multicopy vectors within the transformed host, and unacceptable yields are obtained from those transformants. A promoter should be selected that has maximal strength without significantly reducing plasmid copy number. Generally, a promoter may be considered of at most intermediate strength with respect to a given combination of host, vector and desired protein if the percent of total mRNA in the host corresponding to the promoter is less than 0.3%, and preferably is at most 0.15%.

Ribosome Binding Site—The region of DNA which codes for a site on mRNA which helps the mRNA bind to the ribosome, so that translation can begin. In bacterial expression systems, a ribosome binding site is located after (downstream from) the promoter and before (upstream from) the translational start signal of the DNA sequence to be expressed to produce the desired protein.

Gene—A DNA sequence which encodes, as a template for mRNA, a sequence of amino acids characteristic of a specific polypeptide or protein.

Expression Control Sequence—A DNA sequence that controls and regulates expression of genes when operatively linked to those genes. Such sequences include the lac system, the β-lactamase system, the trp system, the tac, and trc systems, the major operator and promoter regions of phage λ, the control region of fd coat protein, the early and late promoters of SV40, promoters derived from polyoma virus and adenovirus, metallothionine promoters, the promoter for 3-phosphoglycerate kinase or other glycolytic enzymes, the promoters of acid phosphatase, e.g., Pho5, the promoters of the yeast α-mating factors, and other sequences known in the art to control the expression of genes in prokaryotic or eukaryotic cells and their viruses or combinations thereof. For mammalian cells, the gene can be linked to a eukaryotic promoter, such as that for the SV40 early region, coupled to the gene encoding dihydrofolate reductase and selectively amplified in Chinese hamster ovary cells to produce a cell line containing many copies of actively transcribed eukaryotic genes. Those skilled in the art will appreciate that not every expression control sequence listed above as an example may be suitable for use with each host, desired protein and vectors combination.

Percursor of a Protein—A protein with a signal sequence operatively linked to the protein. Typically, the precursor is synthesized within a host cell, e.g., preproinsulin, preserum albumin, prehuman growth hormone, preparathyroid hormone, and preinterferon. In accordance with this invention, a mature protein is obtained by secreting the precursor through the cell membrane of a host with an attendant loss or clipping of the signal sequence of its precursor.

Nucleotide—A monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is called a nucleoside. The base characterizes the nucleotide. The four DNA bases are adenine ("A"), guanine ("G"), cytosine ("C") and thymine ("T"). The four RNA bases are A, G, C and uracil ("U").

DNA Sequence—A linear series of nucleotides connected one to the other by phosphodiester bonds between the 3' and 5' carbons of adjacent pentoses.

Codon—A DNA sequence of three nucleotides (a triplet) which encodes, through messenger RNA ("mRNA"), an amino acid, a translational start signal or a translational termination signal. For example, the nucleotide triplets TTA, TTG, CTT, CTC, CTA and CTG encode for the amino acid leucine ("Leu"), TAG, TAA and TGA are translational stop signals and ATG is a translational start signal.

Plasmid—A non-chromosomal double-stranded DNA sequence comprising an intact "replicon" such that the plasmid is replicated in a host cell. When the plasmid is placed within a host organism, the characteristics of that organism are changed or transformed as a result of the DNA of the plasmid. For example, a plasmid carrying the gene for tetracycline resistance (Tet$^R$) transforms a host cell previously sensitive to tetracycline into one which is resistant to it. A host cell transformed by a plasmid is called a "transformed host" or a "transformant."

Phage or Bacteriophage—Bacterial virus which may include DNA sequences contained in a protein envelope or coat ("capsid").

Cloning Vehicle—A plasmid, phage DNA or other DNA sequence which is able to replicate in a host cell, characterized by one or a small number of endonuclease recognition sites at which its DNA sequence may be cut in a determinable fashion without attendant loss of an essential biological function of the DNA, e.g., replication, production of coat proteins or loss of promoter or binding sites, and which contains a marker suitable for use in the identification of transformed cells, e.g., tetracycline resistance or ampicillin resistance. A cloning vehicle is also known as a vector. In the present invention, the vector must be a "multicopy" vector, i.e., capable of producing multiple copies of itself within the host. Single copy vectors, incapable of producing copies, are not within the scope of this invention.

Host—An organism which on transformation by a cloning vehicle enables the cloning vehicle to replicate and to accomplish its other biological functions, e.g., the production of polypeptides or proteins through expression of the genes of a plasmid.

DNA Signal Sequence—A DNA sequence which encodes, as a template for mRNA, a sequence of typically hydrophobic amino acids at the amino terminus of the polypeptide or protein, i.e., a "signal sequence" or "secretion leader sequence" of the protein. For secretion, such a DNA signal sequence is operatively linked to and located immediately before the DNA sequence of the desired protein and after its translational start signal (e.g., ATG). It is believed that only a portion of a signal sequence of a precursor of a protein is essential for the precursor of the protein to be transported through the cell membrane of a host and for proper clipping of the precursor's signal sequence to free the protein during secretion. Combinations of signal sequences or parts of signal sequences may also be used provided that proper processing takes place in the host. Hence, the term "DNA signal sequence" as used herein includes those DNA sequences that code for that portion of a signal sequence required for secretion.

In accordance with this invention, to obtain expression of a desired protein, an expression system of this invention is operatively linked to a DNA sequence coding for the desired protein and used to transform an appropriate host. The host may then be cultured under appropriate conditions of growth. The desired protein may then be isolated from the culture. Optimum results will, of course, depend on a number of variables, including the appropriate choice of host, promoter, vector, and growth conditions.

Many hosts have been used in recombinant DNA technology and are well known in the art. A wide variety of hosts may be useful in the method of this invention. These hosts include for example, bacteria, such as *E.coli* (for example *E.coli* HB101 or *E.coli.* MC1061), *Bacillus, Streptomyces,* and *Pseudomonas,* fungi, such as yeasts, animal cells, such as CHO cells, mouse, swine, bovine, fowl or fish cells, plant cells in tissue culture, human tissue cells, or other hosts known in the art.

The selection of an appropriate host is controlled by a number of factors recognized by the art. These include, for example, compatibility with the chosen vector, ease of recovery of the desired protein, expression characteristics, biosafety and costs. In the present invention, the host must be able to recognize both the promoter used and the secretion signal sequence used. In addition, the toxicity of the desired protein on the host must be considered, as well as the viability of the host when transformed by a multicopy vector. No absolute choice of host may be made for a particular recombinant DNA molecule or polypeptide from any of these factors alone. Instead, a balance of these factors must be struck with the realization that not all hosts may be equally effective for expression of a particular DNA sequence operatively linked to a particular expression control sequence. While the present invention is not limited to *S. cerevisiae,* yeast is a preferred host, and *S. cerevisiae* is especially preferred.

Various promoters may be used in the expression systems of this invention, provided, however, that the promoter is active in the chosen host and is of at most intermediate strength.

The toxicity of the desired protein to the host affects the promoter choice; for secretion of a less toxic protein, a relatively stronger promoter can be used than for secretion of a more toxic protein. The coding region attached to a promoter in a multicopy vector also affects the strength of the promoter. For example, the pgk promoter is very strong when attached to its own coding region (PGK), but weak when attached to an alpha interferon gene. J. Mellor et al., "Factors Affecting Heterologous Gene Expression in *Saccharomyces cerevisiae,*" *Gene,* 33, pp. 215-26 (1985). In choosing a promoter it should also be appreciated that the junction of a strong promoter to a heterologous gene will considerably weaken the strong promoter, as described by Mellor et al., supra. Because promoter strength is affected by so many variables, the fact that a promoter is too strong for use in one host-vector-desired protein combination does not exclude the use of that promoter in a different combination.

Promoters that may be considered for use in recombinant DNA molecules made from the present invention include, for the yeast *S. cerevisiae,* the promoters of the ACT (actin) gene, the CYC1 (iso-1-cytochrome c) gene and the URA3 gene. Kim and Warner, *J. Mol Biol.,* 165, pp. 79-89 (1983) (mRNA level about 0.008%). For secretion expression systems, strong promoters not suitable for use with *S. cerevisiae* include, for example, the G3PDH and the enolase promoters.

Preferred promoters in secretion expression systems for use with bacteria such as *E.coli* and *B. subtilis* should be of at most intermediate strength. Strong promoters, such as the trp, trc, lac promoters should generally be avoided. Intermediate promoter strength might, however, conveniently be adjusted with regulated promoters, such as the trp or lac promoters, if intermediate inducing growth conditions are chosen.

In the examples, we have used promoters that are active during all phases of growth. If the promoters were to be shut off during growth, the adjustment of vector copy number would presumably not take place unless the promoters were induced. Regulated promoters, however, would probably not provide an advantage. Presumably, turning on a strong promoter in a high-copy secretion construction would immediately lyse the host, as in insulin secretion by *E.coli.*

As discussed above, we have discovered that, for secretion expression systems, a host makes few copies (i.e., low copy numbers) of multicopy vectors if the promoter is strong in the host-vector-desired protein system, and more copies (i.e., higher copy numbers) are made of multicopy vector having a weaker promoter, resulting in improved yields of desired protein. However, the use of a promoter weaker than the CYC1 promoter discussed in Example 3 (e.g., CYC7 or trpl) will not improve yields due to higher copy numbers, because maximal copy numbers are seen for the CYC1 promoter construction (Table 2). Lowest strength promoters are limited by the promoter strength, and the strongest promoters give only limited copy numbers. Though not wishing to be bound by any theory, it appears that high copy numbers combined with strong promoters result in high levels of mRNA, oversecretion of the desired protein or both. In a population of transformants containing cells transformed by vectors containing strong promoters, a mixture of copy numbers occurs in the population. Those cells having high copy numbers with strong promoters will stop growing and eventually lyse, while those transformants with lower copy numbers and the same strong promoter will survive. The population will eventually contain only low copy number transformants. See generally T. J. Silhavy et al., "Mechanisms of Protein Localization," *Microbiol. Res.,* 47, pp. 313-34 (1983).

The multicopy vector and, in particular, the sites chosen therein for insertion of the expression systems of this invention are determined by a variety of factors, e.g., number of sites susceptible to a particular restriction enzyme, size of the protein to be expressed, expression characteristics such as the location of start and stop codons relative to the vector sequences, and other factors recognized by those of skill in the art. The choice of a vector is determined by a balance of these factors, not all selections being equally effective for a given case. The preferred vectors are plasmids, such as those containing origins of replication derived from chromosomal and non-chromosomal DNA. In the yeast *S. cerevisae,* the various ARS- and 2 μ-type vectors (Botstein et al.) are preferred. In *E.coli,* multicopy plasmids, such as ColE1-, pBR322 and RP4 plasmids, or M13 and lambda phage vectors, can be used. For animal cells, non-integrating multicopy vectors, such as vectors based on the bovine papilloma virus, are preferred. The choice of vector will also be influenced by the chosen promoter. Optimal promoter and vector systems will lead to less toxicity of the secreted protein (due to too high copy number or overproduction based on too strong a promoter) and consequently, higher levels of secretion may be obtained.

The heterologous secretion signal sequences of this invention must be recognized and correctly processed by the host. The signal sequence may comprise a naturally occurring signal sequence, an effective portion of a naturally occurring signal sequence, or a combination of two or more signal sequences or effective portions of signal sequences. The signal sequence must be operatively linked to both the promoter and the start signal, ATG. Preferably, the signal sequence begins with the translation start signal. In a preferred embodiment, the signal sequences is selected from signal sequences already used by the host to aid secretion of its own proteins.

The desired protein may include any polypeptide or protein, and may include fusions, preproteins, immature proteins or any desired sequence of amino acids. Preferably, however, desired proteins of this invention include proteins, and other amino acid sequences, that are secretable by some micro-organism or cell. Examples of such secretable proteins and other amino acid sequences include serum proteins, analgesic polypeptides such as β-endorphin, somatostatin, insulin, growth hormone (human and bovine), luteinizing hormone, ACTH, pancreatic polypeptide preproteins, preproinsulin, proinsulin, and the A and B chains of insulin. The desired proteins of the present invention may comprise proteins and other amino acid sequences naturally secreted into the medium by the selected host.

The desired protein of the present invention need not be secreted by the selected host. As will be seen in Example 6, the host need only manufacture the desired protein operatively linked to the chosen signal sequence and correctly process the desired protein into the lumen of endoplasmic reticulum. If the desired protein enters the secretion pathway of the host, benefits may be obtained for the desired protein, such as glycosylation. Secretion is, however, the preferred result for the desired protein.

The present invention may be useful in mammalian cells, if non TM integrating, multicopy vectors, such as vectors derived from bovine papilloma virus (D. DiMaio et al., "Bovine Papilloma-Virus Vector that Propagates as a Plasmid in Both Mouse and Bacterial Cells," *Proc. Nat. Acad. Sci. USA*, 79, pp. 30-34 (1982)) are used in conjunction with an intermediate strength promoter.

The following, non-limiting examples will serve to further illustrate the present invention.

EXAMPLE 1

Preparation Of MFα1/SMC DNA Sequences

This example describes the preparation of a transformed yeast which is used in a later example for comparative purposes. The transformed yeast of this example has a plasmid containing a MFα1 promoter (which is a strong promoter in yeast as shown below) operatively linked to a MFα1 secretion leader and a DNA sequence coding for SMC. Other examples describe the substitution of the ACT and CYC1 promoters for the MFα1 promoter, and a comparison of the secretion levels of the variously transformed yeasts. In addition, other examples describe the preparation of transformed yeasts having plasmids characterized by DNA sequences coding for desired proteins other than SMC.

We first isolated the gene for pre-MFα1 and its associated expression control systems and we then operatively linked the MFα1 promoter and signal sequence to a DNA sequence for SMC.

The DNA sequence coding for the precursor of MFα1 has been sequenced by J. Kurjan and I. Herskowitz, "Structure of a Yeast Pheromone Gene (MFα): A Putative α-Factor Precursor Contains Four Tandem Copies of Mature α-Factor," *Cell*, 30, pp. 933-43 (1982). We isolated the gene coding for those pre-MFα1 and its associated expression control sequences from *S. cerevisiae* using the library constructed by K. A. Nasmyth, and S. I. Reed, "Isolation of Genes by Complementation in Yeast: Molecular Cloning of a Cell-Cycle Gene," *Proc. Natl. Acad. Sci. USA*, 77, 2119-23 (1980). Instead of using the cdc28 mutant described in Nasmyth and Reed for isolation and cloning of the cdc28 gene, we used the following oligonucleotide corresponding to amino acids 97 to 102 of the published pre-MFα1:

(5') GTA CAT TGG TTG C/GCC G/A/TGG (3')

The MFα1 secretion precursor, comprising a secretion leader and four MFα1 repeats is shown in FIG. 1A. The stippled regions indicate spacer regions between the MFα1 repeats. Before substituting a desired heterologous protein for the four MFα1 repeats, as shown in FIG. 1B, the pre-MFα1 gene and associated expression control sequence, which resided on a 1.7 kb EcoRI fragment, were subcloned into pUC18, the selected cloning vector. The resulting plasmid (p220/3) now included an MFα1 promoter, an MFα1 signal sequence and an MFα1 DNA coding sequence. In order to isolate the MFα1 coding sequence, we subjected plasmid p220/3 to mutagenesis using the procedure described in B. A. Oostra et al., "Transforming Activity of Polyoma Virus Middle-T Antigen Probed by Site-Directed Mutagenesis," *Nature*, 304, pp. 456-59 (1983). As a result of the mutagenesis, a convenient BglII site was introduced at the junction between the secretion leader and the coding sequence for the repeats in the MFα1 DNA sequence as follows:

```
modified
oligomer:  (3') TA TTT TCT CTA GAA CTT CGA ACC (5')

original:  (3') TA TTT TCT CTC CGA CTT CGA ACC (5')
sequence         lys arg glu ala glu ala trp
```

The resulting plasmid was called p254 (FIG. 2). It was further modified to prevent unintended cleavage at a BglII site found at the 5' end of the MFα1 promoter. We altered this undesired BglII site by cleaving with BglII and filling in the protruding ends using the large (Klenow) fragment of DNA polymerase I and deoxynucleotide triphosphates and subsequent ligation using T4 ligase. To allow for a different cleavage in the plasmid (Examples 5 and 6), a StuI site was introduced, in a procedure similar to the mutagenesis described above, at the position corresponding to the same lys-arg cleavage site:

```
modified
oligomer: (5') TA AAA AGG CCT CTT GAA GC (3')

BglII-sequence: (5') TA AAA AGA GAT CTT GAA GC (3')
                       lys  arg
```

We then made a MFα1/SMC (secretion leader/desired protein) fusion by inserting a 500 bp HindIII fragment carrying a synthetic SMC gene starting with a unique NcoI site into the HindIII site of plasmid p254 (described above) which contained the MFα1 promoter and secretion leader and obtained plasmid F-9 as shown in FIG. 2. The synthetic SMC gene is described in G. Buell et al., "Optimizing the Expression in *E.coli* of a Synthetic Gene Encoding Somatomedin-C (IGF-1)," *Nucl. Ac. Res.*, 13, pp. 1923-38 (1985). We then cut plasmid F-9 with BglII and NcoI, with simultaneous S1 treatment and religation to remove the Δ portion of plasmid F-9 and obtain pS30/25, shown in FIG. 2. The correct fusion of the MFαl secretion leader and the SMC structual DNA sequence had the following sequence (glycine is the first amino acid of SMC):

(secretion leader)-AAA—AGA—GGT—CCA—(SMC)
                  lys   arg   gly   pro As a result the SMC DNA sequence was operatively linked to the MFαl secretion leader so that the SMC protein would be properly secreted by yeast.

Figure 3A:
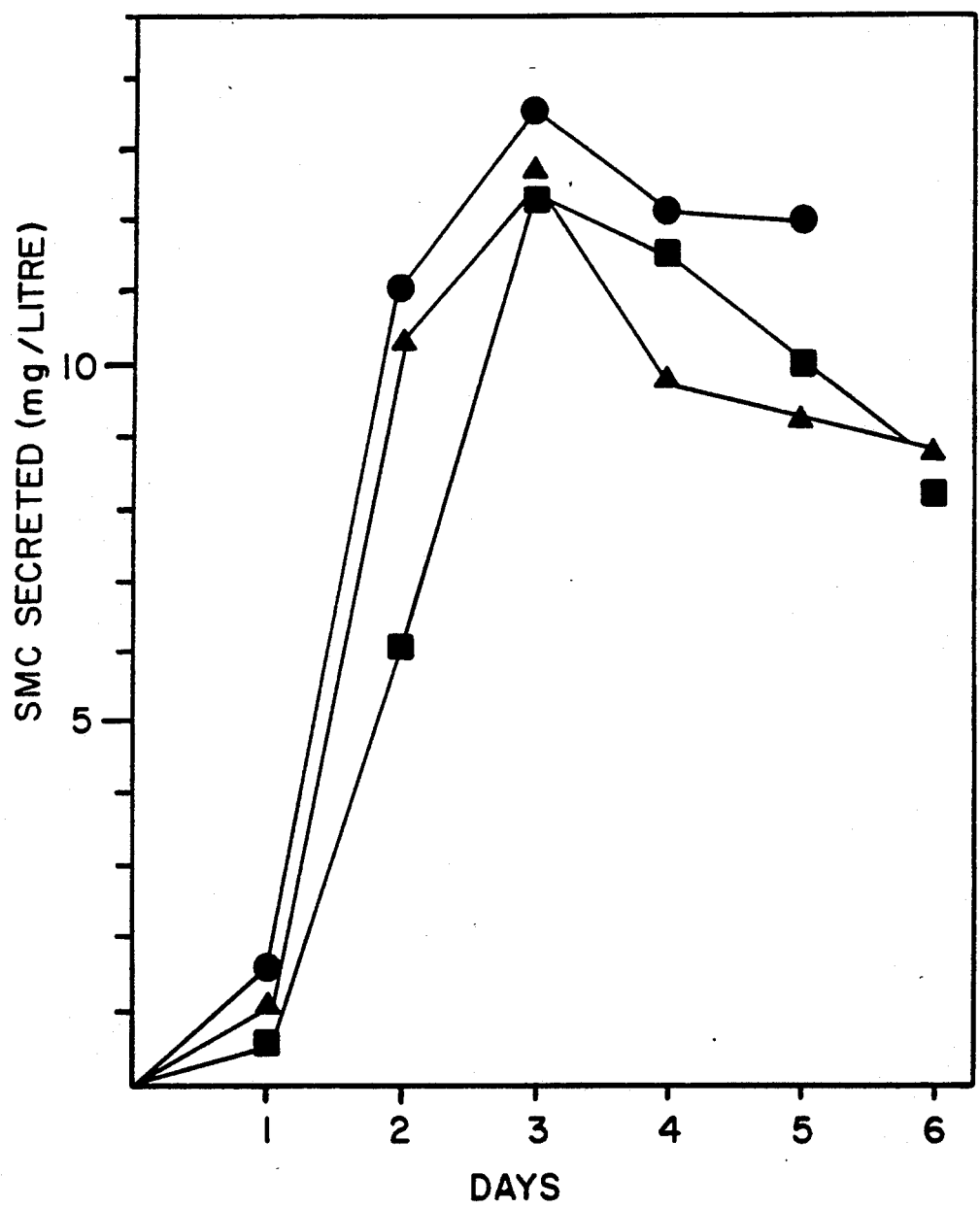
FIGS. 3A and 3B show two graphs.
Figure 3B:
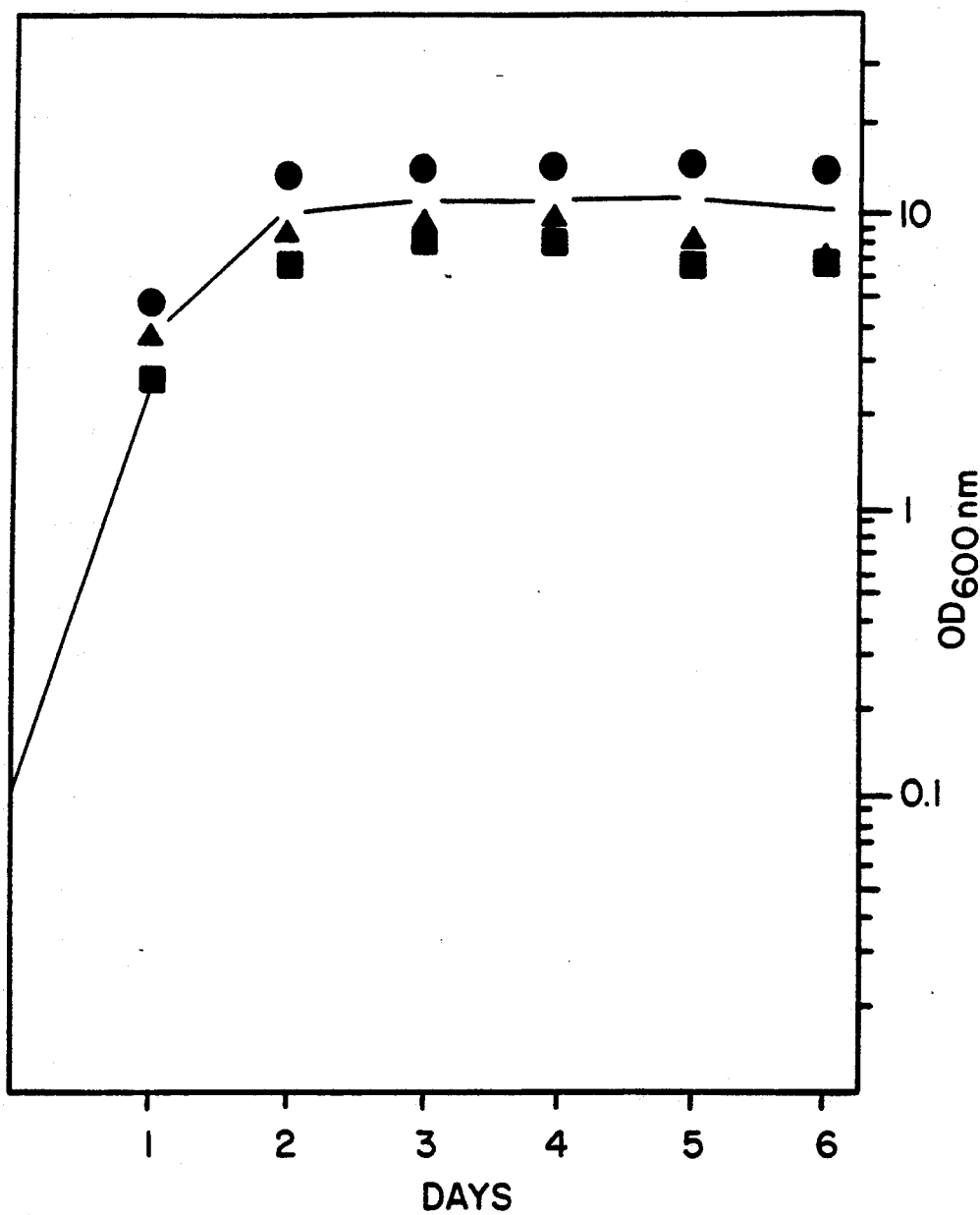

As outlined in FIG. 2, we introduced the MFαl/SMC fusion into a yeast shuttle vector carrying origins of replication for *E.coli* and yeast (ori and the 2 μ origin of replication, respectively), as well as selectable markers for both organisms (*E.coli*: bla; yeast: URA3). SMC secretion rates by *S. cerevisiae* transformed with this expression vector are shown in FIG. 3A.

EXAMPLE 2

Preparation Of ACT/MFαl/SMC DNA sequences

The DNA sequence encoding actin in yeast is described in D. Gallwitz and I. Sures, "Structure of a Split Yeast Gene: Complete Nucleotide Sequence of the Actin Gene in *Saccharomyces cerevisiae*," *Proc. Natl. Acad. Sci. USA*, 77, pp. 2546–50 (1980). Levels of the mRNA coding for actin (D. Gallwitz et al., "The Actin Gene in the Yeast *Saccharomyces cerevisiae*: 5' and 3' End Mapping, Flanking and Putative Regulatory Sequences," *Nucl. Ac. Res.*, 9, pp. 6339–50 (1981)) suggest that the ACT promoter is a promoter of intermediate strength, see Table 1. See also Himmelfarb, supra.

Figure 4A:
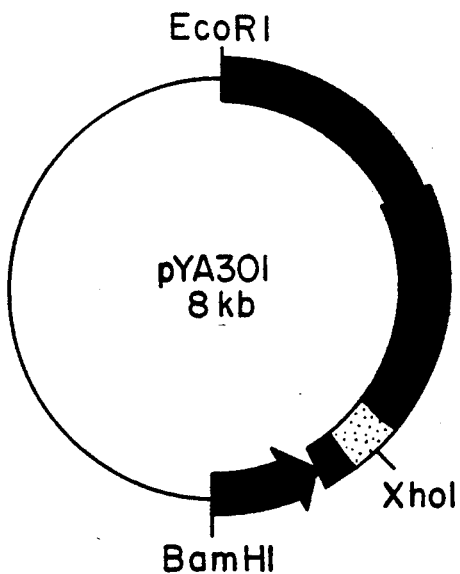
FIG. 4A shows the construction of actin promoter fragments ending in EcoRI sites.
Figure 4B:
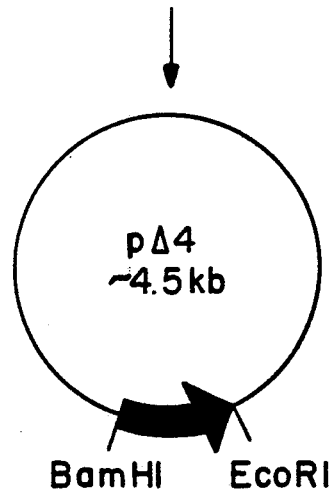
FIG. 4B shows the DNA structure of promoter ends for actin and the pEX-5, pEX-7, and pEX-8 vectors.

In order to use the ACT promoter in the constructions of this and the following examples, we placed convenient restriction sites at the end of the promoter. Plasmid pYA301, shown in FIG. 4, contains the ACT gene and its associated expression control sequences on a 4 kb EcoRI-BamHI fragment. Plasmid pYA301 is a 4 kb EcoRI-BamHI subclone of pYA208 (Gallwitz and Sures, supra) inserted into pBR322. We cut plasmid pYA301 at the single XhoI site and treated it with Bal31. Following an empirically determined time of Bal31 treatment, we cut the plasmid with EcoRI and its protruding ends were filled in using the large (Klenow) fragment of DNA polymerase I. Finally, the treated plasmid was religated under dilute conditions. Approximately half of the resulting plasmids, identified collectively as pΔ4, contained an EcoRI site. These EcoRI sites had been formed by joining the filled-in EcoRI end to the Bal31 ACT promoter end. Structures of various pΔ4 promoter ends in the vicinity of the ATG start codon of the religated plasmid are shown in FIG. 4B.

To operatively link the isolated ACT promoter to the MFαl signal sequence SMC fusions, we matched the 3' end of the ACT promoter to the amino terminal end of the MFαl/SMC fusion. We accomplished this by introducing an EcoRI site upstream (i.e., earlier in the transcription reading direction) of the ATG start codon of the MFαl secretion leader by carrying out the following mutagenesis using the procedure described in Oostra et al., supra:

modified oligomer:

(5') A ATA TAA AC<u>G AAT TC</u>A AGA ATG AG (3')

original sequence:

-continued
(5') A ATA TAA ACG ACC AAA AGA ATG AG (3')

We named the resulting plasmid p269/20.

Figure 5:
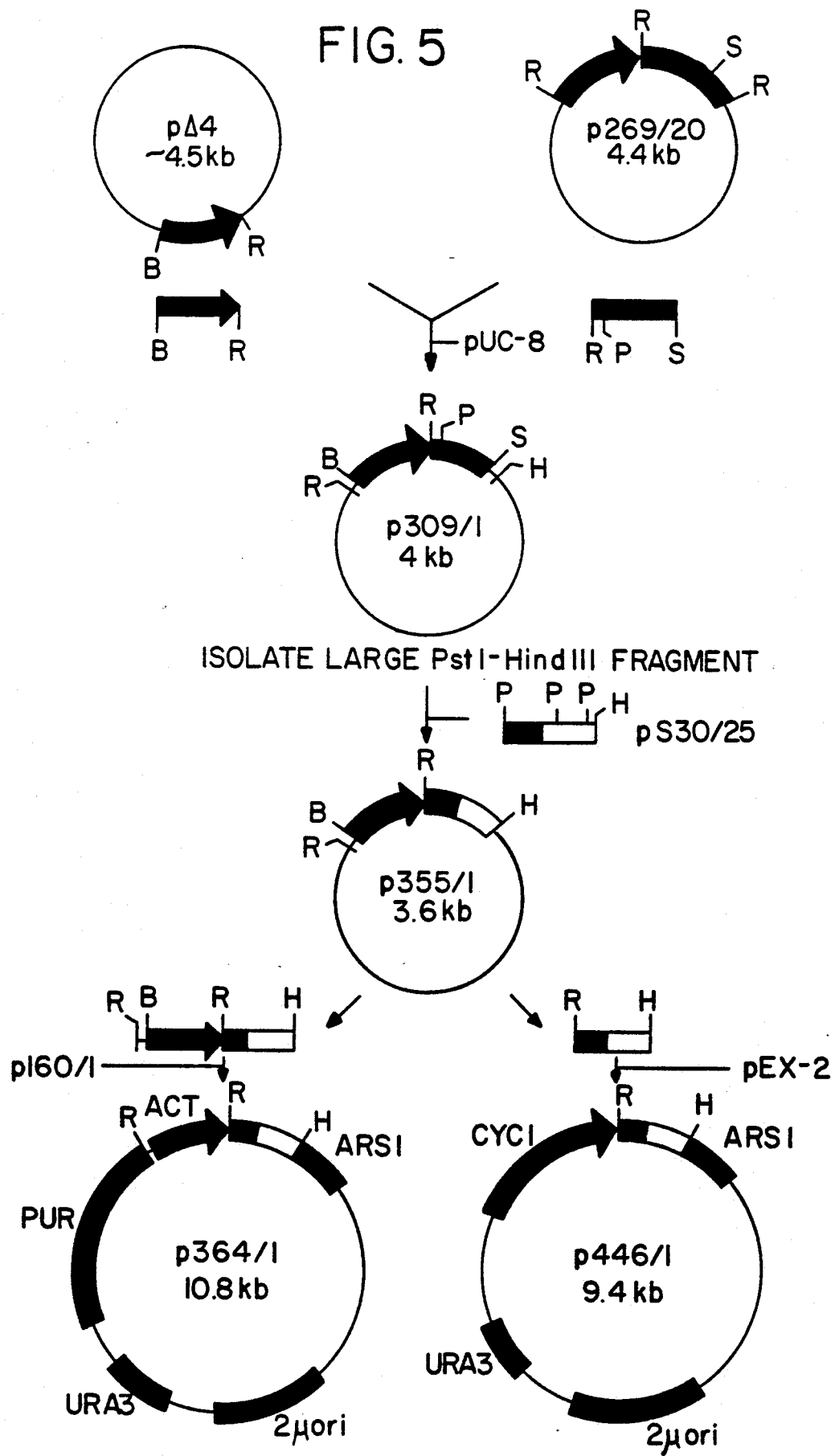
FIG. 5 shows the construction of SMC secretion vectors based on the ACT and CYC1 promoters.

We joined the BamHI-EcoRI fragment of pEX-7 (FIG. 4) isolated above and containing the ACT promoter to the EcoRI-SalI fragment of plasmid p269/20 (which carried the MFαl secretion leader) and inserted the fragment into a BamHI and SalI cut pUC8 vector as shown in FIG. 5. We further modified the resulting plasmid (p309/1) by replacing the MFαl secretion leader region of plasmid p309/1 by the secretion leader region, joined to the SMC gene, of plasmid pS30/25. Plasmid pS30/25 is shown in FIG. 2. The modification was carried out by cutting plasmid p309/1 with PstI and HindIII. The large fragment was isolated and joined to a fragment of pS30/25 resulting from partial digestion of that plasmid with PstI and HindIII. The resulting plasmid, p355/1, (ACT promoter/MFαl secretion leader/SMC structural DNA sequence) was transferred to a yeast shuttle vector, as shown in FIG. 5, which resulted in formation of plasmid p364/1. SMC secretion rates by yeast transformed with this plasmid are shown in FIG. 3A.

EXAMPLE 3

Preparation Of CYC1/MFαl/SMC Plasmids

Under inducing conditions, iso-1-cytochrome c (CYC1) amounts to approximately 0.2% of the total cellular protein of yeast, and the encoding mRNA amounts to about 0.05% of the total poly(A) RNA. R. S. Zitomer and B. D. Hall, "Yeast Cytochrome c Messenger RNA. In Vitro Translation and Specific Immunoprecipitation of the CYC1 Gene Product," *J. Biol. Chem.*, 251, 6320–26 (1976). The CYC1 promoter is thus a weak promoter.

In order to construct a CYC1 promoter/MFαl secretion leader/SMC coding sequence, we isolated an EcoRI-HindIII fragment carrying the MFαl secretion leader correctly fused to the SMC gene from plasmid p355/1, which is shown in FIG. 5. We inserted this fragment between the EcoRI and HindIII sites of pEX-2 to obtain plasmid p446/1 (See FIG. 5).

pEX-2 is described in J. F. Ernst and R. C. Chan, "Characterization of *S. cervisiae* Mutants Supersensitive to Aminoglycoside Antibiotics," *J. Bacteriol.*, 163, pp. 8–14 (1985).

The vector p446/1 expressed the MFαl/SMC fusion under the control of the CYC1 promoter. SMC secretion rates from yeast transformed by this vector are shown in FIG. 3A.

EXAMPLE 4

Comparison Of Secretion Of SMC Using The MFαl, ACT And CYC1 Promoters With Both The URA3 Gene And The LEU2 Gene on Expression Vectors The construction of tripartite SMC expression vectors based on the MFαl secretion leader and the MFαl, the ACT, and the CYC1 promoters has been described above. Each of these vectors contained the yeast URA3 gene for selection in yeast. We also constructed vectors based on selection using the yeast LEU2 gene. The expression of the plasmid LEU2 gene is low due to a partial deletion; higher copy numbers of the LEU2 type expression vectors are needed to allow the growth of transformants on leucine-free media. E. Erhart and C. P. Hollenberg, "The Presence of a Defective LEU2

Gene on 2μ DNA Recombinant Plasmids of *Saccharomyces cervisiae* is Responsible for Curing and High Copy Number," *J. Bacteriol.*, 156 pp. 625-35 (1983). For a discussion of the use of yeasts having the URA3 gene or the LEU2 gene in recombinant DNA experiments, see D. Botstein et al., "Sterile Host Yeast (SHY): a Eukaryotic System for Biological Containment for Recombinant DNA Experiments," *Gene*, 8, pp. 17-24 (1979).

Figure 6:
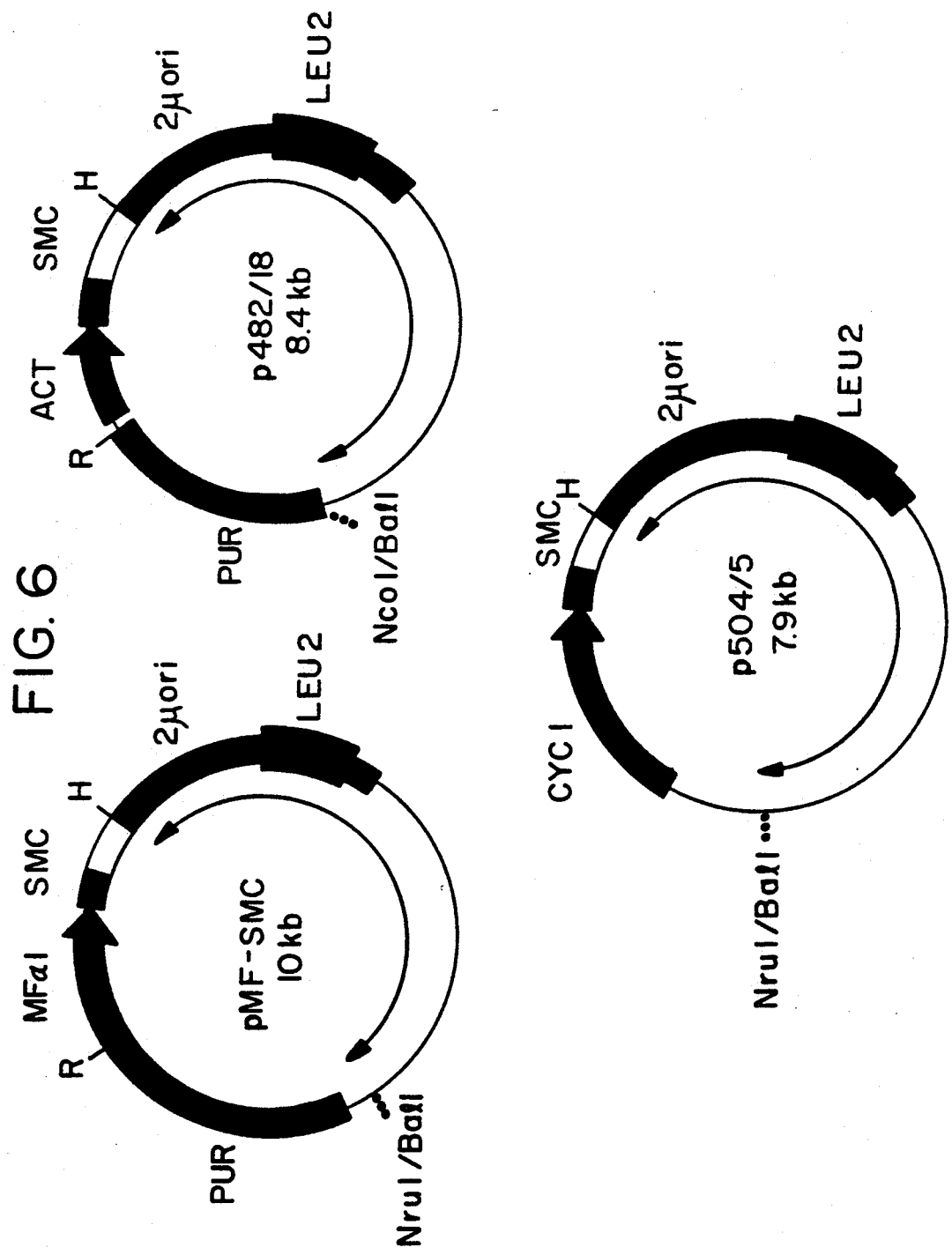
FIG. 6 shows the structure of SMC secretion vectors based on the yeast LEU2 gene.

We constructed the LEU2-type vectors by inserting the chosen promoter/MFαl secretion leader/SMC structural sequence into plasmid pJDB207, using procedures similar to those used with the URA3 plasmids. The structures of the resulting plasmids are shown in FIG. 6. The plasmid pJDB207 is described in J. D. Beggs, "Multiple-copy Yeast Vectors," *Molecular Genetics in Yeast, Alfred Benzon Symposium* 16, 383-95 (1981).

We transformed the three URA-type vectors derived from plasmid pEX-2 (which is described in J. F. Ernst and R. C. Chan, supra) and the three LEU2-type vectors into yeast strain BJ1991. We deposited two of the recombinant yeast strains in the Deutsche Sammlung Von Mikroorganismen (West German Culture Collection). One strain, YE439, is a LEU2-type vector with the ACT promoter/MFαl secretion leader/SMC structural sequence. It was deposited on Oct. 30, 1985 and is identified as DSM 3578. Another strain, YE466, is a LEU2-type vector with the CYC1 promoter/MFαl secretion leader/SMC structural sequence. It was deposited on Oct. 30, 1985 and is identified as DSM 3579. Transformants were grown in the "SD" medium described in F. Sherman et al., "Methods in Yeast Genetics," Cold Spring Harbor Laboratory, Cold Spring Harbor, N.Y. (1981), containing tryptophan and leucine (for URA3-type vectors), or tryptophan and uracil (for LEU2-type vectors) to an optical density of 2 at 600 nm. We used these cultures to inoculate production medium, consisting of SD medium containing 4% casamino acids and tryptophan (inoculum was 10% of final volume of production medium). At appropriate times during growth, 0.5 ml of the cultures were pelleted using a microfuge. We redissolved the cell pellets in 1/10 the original culture volume by boiling 5 min in sodium dodecyl sulphate (SDS) sample buffer, which is described in U. K. Laemmli, "Cleavage of the Structural Proteins During the Assembly of the Head of Bacteriophage T4," *Nature*, 227, pp. 680-85 (1970). We then determined the SMC levels in the redissolved cell pellets and in the culture fluid after dilution, using a radioimmune assay (Nichols Institute Diagnostics, San Juan Capistrano, Calif.).

With all six constructions, less than 10% of the total SMC was cell associated. We purified SMC present in the culture medium, and analyzed it, finding that the amino terminal and carboxyl terminal amino acids were identical to human SMC and that the biological activity of the secreted SMC was the same as human SMC.

Figure 7A:
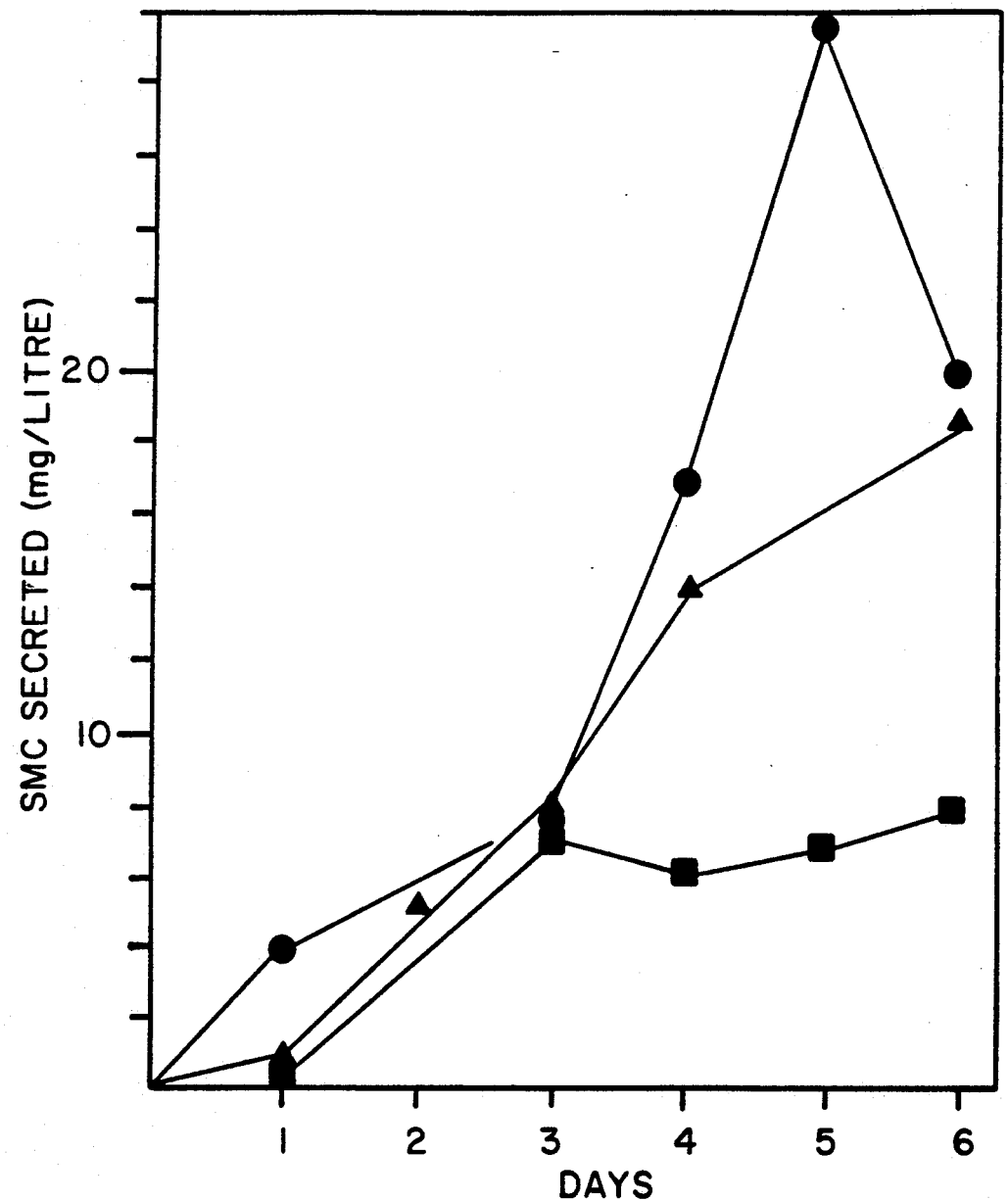
FIGS. 7A and 7B show two graphs.
Figure 7B:
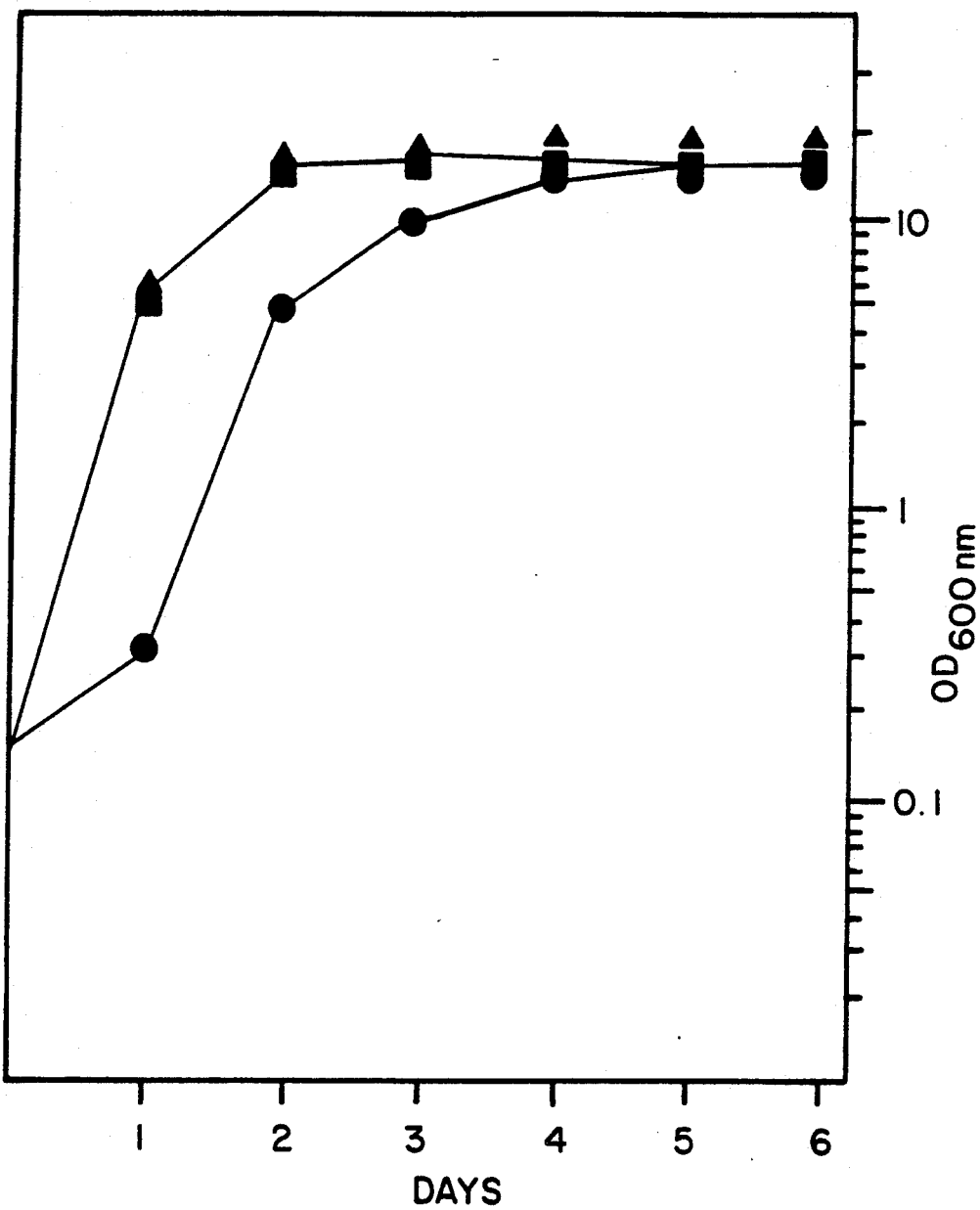

Surprisingly, the weakest promoter used, CYC1, resulted in the highest SMC secretion values shown in FIGS. 3A and 7A and Table 2. This was unexpected because the strongest promoter would have been expected to give the highest secretion values. Unexpectedly, the transformants carrying the CYC1 constructions grew slowest and showed a pronounced optimum curve of SMC secretion, indicating the occurrence of cell lysis and SMC degradation (see FIG. 7A and 7B).

To determine the reason for the unexpected results, we analyzed SMC plasmid copy number and transcript levels in the transformants described herein after three days in production medium. The results are shown in Table 2. We discovered an inverse relationship between copy number and promoter strength in secretion systems. The secretion system with the weakest promoter (CYC1) proved to have the highest copy numbers. The MFαl constructs had the lowest copy numbers. The average SMC transcript level proved to be proportional to copy numbers for both URA3 and LEU2 constructs. In turn, with LEU2 constructions, mRNA levels were proportional to secretion levels. With URA3 constructions, no significant increase of SMC secretion levels with increased mRNA was observed. While not wishing to be bound by theory, the URA3 constructs do not appear to have the same effect on the SMC secretion levels because of a high percentage of URA3 plasmid loss.

A high percentage of URA3 transformants actually have few or no URA3 expression plasmids. These unproductive transformants contribute little to overall SMC secretion. Conceivably, a high percentage of URA3 transformants also have high copy numbers. These transformants would contribute little to SMC secretion because of slow growth and reduced cell viability. This suggested mechanism does not apply to LEU2 vectors because the minimum copy number of the LEU2-type vectors in transformants grown in leucine-free media is about 35 (Erhart and Hollenberg, supra). In addition, since the production medium used contains leucine (but no uracil), elevated copy numbers are not required for growth of LEU2 vector-transformants in this medium. Thus, yeast strains transformed with LEU2 appear more homogeneous than URA3 vectors with respect to copy number and mRNA content.

Transformation frequencies for all six plasmid constructions are also shown in Table 2. Approximately similar transformation frequencies were obtained with all the URA3-type vectors. However, dramatic differences were seen for the LEU2-type vectors; the MFαl promoter constructions could not be transformed in yeast at all, relatively high frequencies were observed for the ACT promoter construction and lower frequencies of transformation, compared to the control (pJDB207) and the ACT construction, were characteristic of the CYC1 construction. We did obtain one rare LEU2-type vector transformant with the MFαl construction; however, this transformant contained a rearranged plasmid that directed the synthesis of low amounts of SMC as shown parenthetically in Table 2. This result suggests that the MFαl promoter does not permit a sufficiently high copy number to overcome the effects of the LEU2 defect.

Thus, secretion rate, cell viability, promoter strength and vector copy number appear to be interrelated.

TABLE 2

| Construction | plasmid | promoter | selection | transformants/μg | % loss | copy number | RNA* | SMC (mg/l) |
|---|---|---|---|---|---|---|---|---|
| 1 | p336/1 | MFαl | URA3 | 225 | 6 | 27 | 10.9 | 12 |
| 2 | p364/1 | ACT | URA3 | 319 | 10 | 32 | 26.3 | 12 |
| 3 | p446/1 | CYC1 | URA3 | 296 | 12 | 49 | 40.2 | 13 |
| — | p160/1 | control | URA3 | 300 | 10 | 45 | — | — |

TABLE 2-continued

| Construction | plasmid | promoter | selection | transformants/μg | % loss | copy number | RNA* | SMC (mg/l) |
|---|---|---|---|---|---|---|---|---|
| 4 | (pMF-SMC) | MFα | LEU2 | 0(1) | (32) | (41) | (8.2) | (8) |
| 5 | p482/18 | ACT | LEU2 | 4 | 0 | 69 | 31.9 | 20 |
| 6 | p504/5 | CYCl | LEU2 | 2 | 0 | 110 | 54.8 | 28 |
| — | p-JDB-207 | control | LEU2 | 58 | 0 | 110 | — | — |

*A value of 1 indicates SMC mRNA content equal to an internal control probe (actin transcript).
Numbers are for comparative purposes only.

EXAMPLE 5

Secretion of TNF

We constructed fusions of the MFα secretion leader to the gene encoding human tumor necrosis factor (TNF) as shown in FIG. 8 by using the procedure described above for MFα/SMC fusions. We then analyzed the effect of promoter replacement on TNF secretion.

We ligated the following three fragments to construct vector pTNFll (see FIG. 8): (1) a 1.2 kb EcoRI-StuI fragment carrying the promoter and the secretion leader of MFα ending in a StuI site (described supra); (2) a 9 kb EcoRI.HindIII fragment of pEX-2 carrying the yeast 2μ origin of replication and the URA3 gene for selection in yeast (described supra); and (3) a blunt-ended HindIII fragment (0.9 kb) carrying the TNF gene. Isolation procedures for this third fragment are disclosed in D. Pennica et al., "Human Tumor Necrosis Factor: Precursor Structure, Expression and Homology to Lymphotoxin," *Nature*, 312, pp. 724–29 (1984). We generated the blunt-ended HindIII fragment by using synthetic oligonucleotide linkers to recreate the 5' end of the TNF gene by extension from an AvaI site situated close to the 5' end of the TNF gene (valine is the first amino acid of TNF). The junction of MFα to the TNF gene had the following sequence:

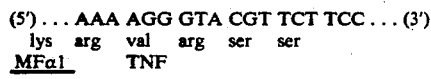

```
(5') ... AAA AGG GTA CGT TCT TCC ... (3')
     lys  arg val arg ser ser
     MFα            TNF
```

The construction of a TNF secretion vector based on the ACT promoter, instead of the MFα promoter, is also shown in FIG. 8. We ligated the following fragments to construct pACT-TNF-EX: (1) a 1.2 kb PstI-HindIII fragment from pTNFll carrying most of the MFα secretion leader fused to the TNF gene (described supra); (2) a 0.5 kb BamHI-PstI fragment from p355/1, shown in FIG. 5, carrying the ACT promoter and part of the MFα leader (described supra); and (3) the 9 kb BamHI-HindIII fragment of pEX-2 (described supra).

We transformed yeast strain BJ1991 with pTNFll or pACT-TNF-EX and selected for Ura+ prototrophs. Transformants were grown selectively in liquid SD medium lacking uracil. Shake flasks containing YPD medium, which is disclosed in F. Sherman et al., supra, were inoculated with minimal cultures (10% final volume) and incubated at 30° C. on a rotatory shaker. At appropriate times during incubation, we centrifuged 1 ml samples of the yeast culture for 1 min using a microfuge. We then treated the cell pellet with zymolase to generate spheroplasts. We then lysed the spheroplasts using 1% triton X-100 at 20% of the original culture volume, followed by removal of cell debris by a short centrifugation step.

We electrophoresed samples containing TNF on 12.5% SDS-acrylamide gels and transferred the proteins to nitrocellulose by standard methods. We probed the protein blot with rabbit antibodies for human TNF, and we visualized regions of the blot containing TNF/anti-TNF complexes using peroxidase-coupled swine anti-rabbit antibodies. Maximal TNF expression results in the culture fluid and in cell extracts are shown in Table 3. The results indicated that a significant improvement of secretion of TNF was obtained when the MFα promoter was replaced by the ACT promoter. Only 10–20% of the total TNF produced was cell associated.

TABLE 3

| MAXIMAL TNF EXPRESSION LEVELS BY YEAST TRANSFORMANTS | | |
|---|---|---|
| plasmid | cells (mg/liter) | medium (mg/liter) |
| pTNFll | 1 | 5 |
| pACT-TNF-Ex | 1.5 | 15 |

EXAMPLE 6

Secretion of TPA

The gene coding for human tissue plasminogen activator (TPA) carries a convenient BglII site at a position corresponding to the first amino acid of TPA. D. Pennica et al., "Cloning and Expression of Human Tissue-type Plasminogen Activator cDNA in *E.coli*," *Nature*, 301, pp. 214–21 (1983). In order to allow correct fusion to the MFα secretion leader, we introduced a convenient BglII site at the MFα position corresponding to the lys-arg junction. The structure of the MFα/TPA fusion point in the following constructions is as follows:

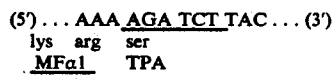

```
(5') ... AAA AGA TCT TAC ... (3')
     lys arg ser
     MFα      TPA
```

Figure 9:
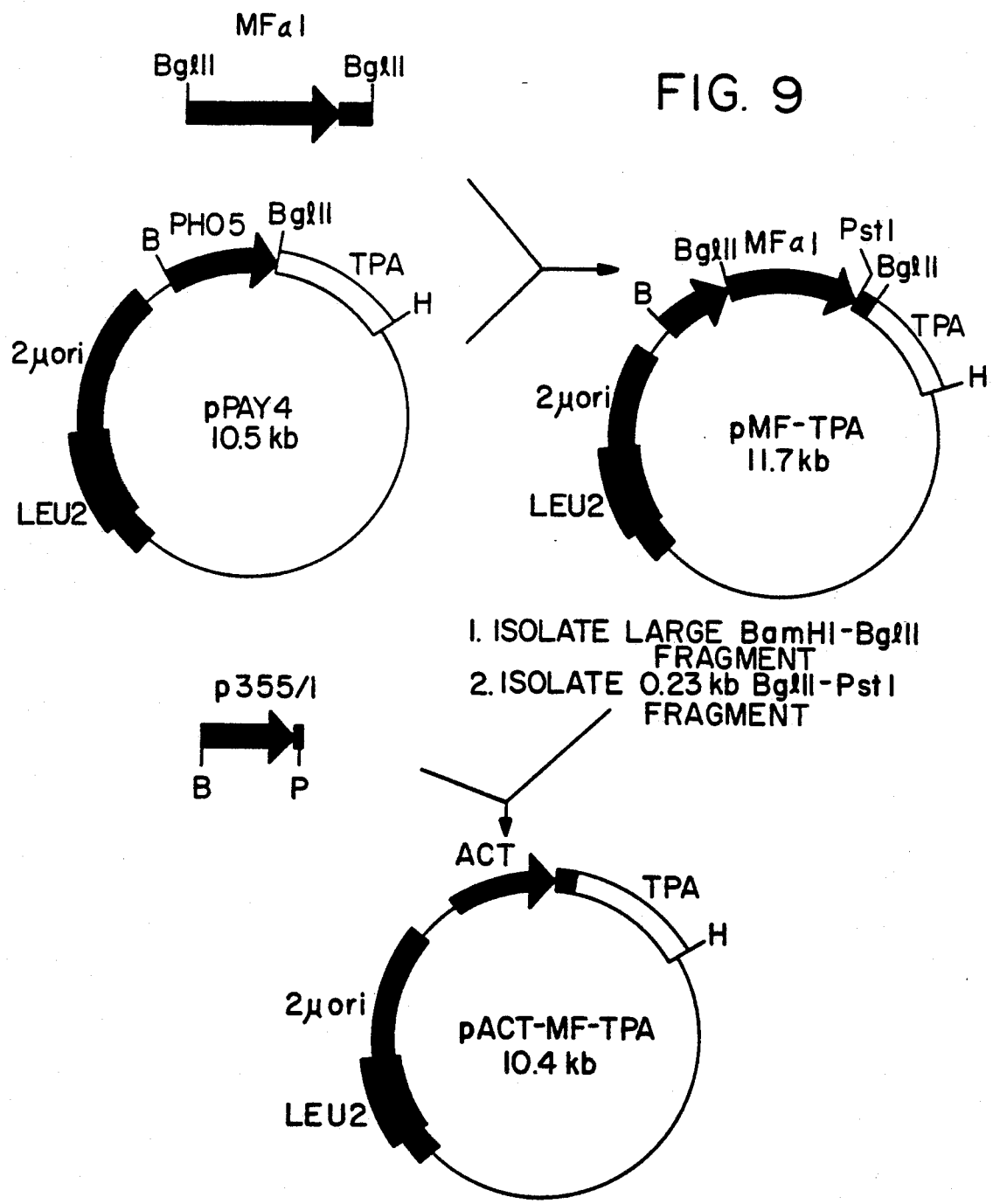
FIG. 9 shows the construction of secretion vectors for TPA.

We inserted a BglII fragment carrying the MFα promoter and secretion leader into the single BglII site of the previously constructed vector pPAY4 as shown in FIG. 9. In this manner, the PH05 promoter and secretion leader were replaced by the MFα promoter and secretion leader. We further modified the resulting expression vector, pMF-TPA, by replacing the PH05 and MFα promoters by the ACT promoter, as shown in FIG. 9, to obtain expression vector pACT-MF-TPA. The PH05 promoter present in both TPA constructions is repressed in regular (high-phosphate) production media. Accordingly, the expression results described below are due to the activity of the MFα promoter because the tests were carried out in regular (high phosphate) media.

We used each of the expression plasmids, pACT-MF-TPA and pMF-TPA, to transform yeast cells of strain BJ1991, as described above, selecting for LEU+ prototrophs. We selectively grew transformants in SD medium. We inoculated shake flasks containing YPD medium with the SD cultures (10% of final volume) and incubated at 30° C. At appropriate times during incubation, we prepared cell extracts as described above in Example 4.

We determined TPA activity in cell fractions by halo formation on fibrinogen-plasminogen-agar plates as described in A. Granelli-Piperno and E. Reich, "A Study of Proteases and Protease-Inhibitor Complexes in Biological Fluids", *J. Exp. Med.*, 148, pp. 223-34 (1978). The results shown in Table 4 indicate that replacement of the MFα1 promoter by the ACT promoter is advantageous in obtaining secretion of heterologous proteins by yeast using alpha mating factor fusions.

TABLE 4

| | MAXIMAL TPA EXPRESSION LEVELS BY YEAST TRANSFORMANTS | |
|---|---|---|
| plasmid | cells (μg/liter) | medium (μg/liter) |
| pMF-TPA | 30 | 0 |
| pACT-MF-TPA | 100 | 5 |

As shown in Table 3, most of the TPA produced was cell associated; only 5% of the total TPA produced appeared in the medium. However, the following evidence suggested that yeast TPA had entered the secretion pathway:

(1) the TPA expressed was biologically active, indicating correct folding. Attempts to express TPA in yeast without a secretion signal sequence produced non-active TPA; and (2) the cell associated TPA was glycosylated. Secretion at least into the lumen of the endoplasmic reticulum is necessary for glycosylation to occur.

It will be apparent to those skilled in the art that various modifications may be made in the invention without departing from its spirit or scope, and our basic construction can be altered to provide other embodiments which utilize the processes and compositions of this invention. Therefore, it will be appreciated that the scope of this invention is to be defined by the claims appended hereto rather than the specific embodiments which have been presented as examples.

What is claimed is:

1. A DNA sequence comprising:
   (a) a yeast promoter selected from the group consisting of the ACT and CYC1 promoters, and
   (b) a heterologous yeast secretion signal sequence operatively linked to said promoter.

2. The DNA sequence according to claim 1, wherein (b) is the MFα1 secretion signal sequence.

3. A DNA sequence according to claim 2, further comprising a DNA sequence coding for a desired protein operatively linked to said DNA secretion signal sequence.

4. The DNA sequence of claim 3, wherein said desired protein is capable of being secreted by a microorganism or cell.

5. The DNA sequence of claim 3, wherein said desired protein is selected from the group consisting of serum proteins, analgesic polypeptides, β-endorphin, somatostatin, SMC, insulin, human growth hormone, bovine growth hormone, luteinizing hormone, ACTH, pancreatic polypeptide preproteins, RPA, TNF, preproinsulin, proinsulin, the A chain of insulin and the B chain of insulin.

6. A multicopy expression vector comprising a DNA sequence according to any one of claims 1 to 5.

7. The multicopy expression vector of claim 6, wherein said multicopy expression vector is a plasmid.

8. A unicellular host transformed by a DNA sequence according to any one of claims 1-5.

9. A unicellular host transformed by a multicopy expression vector according to claim 6.

10. A unicellular host transformed by a plasmid according to claim 7.

11. A unicellular host according to claim 10, wherein said plasmid is an ARS-type plasmid or a 2μ-type plasmids.

12. A unicellular host according to claim 8, wherein said host is a yeast.

13. A unicellular host according to claim 12, wherein said host is *Saccharomyces cerevisiae*.

14. A method for producing a desired protein, comprising culturing a transformed host which has been transformed with a vector comprising the DNA sequence of any one of claims 3-5.

* * * * *

UNITED STATES PATENT AND TRADEMARK OFFICE
CERTIFICATE OF CORRECTION

Page 1 of 2

PATENT NO. : 5,082,783
DATED : January 21, 1992
INVENTOR(S) : Ernst, et. al.

It is certified that error appears in the above-indentified patent and that said Letters Patent is hereby corrected as shown below:

Title page, item [56], col. 2, line 13, under OTHER PUBLICATIONS--"cerervisi" should be --cerevisiae--;
line 21, after "77," insert --pp.--;
line 25, "Acitivity" should be --Activity--;
Column 3, of Title page, col. 2, line 1, delete "vol.". (OTHER PUBLICATIONS)
Column 1, line 9, After"Promoters" insert comma --,--.
Column 2, line 67, "$p336/1$" should be --p446/1--.

Column 3, line 2, "$p446/1$" should be --p336/1--;
line 15, "504/1" should be --504/5--.

Col. 5, line 41, "vectors" should be --vector--.

Col. 9, line 2, "sequences is" should be --sequence is--;
line 31, delete "TM" and insert hyphen -- - --.

Col. 10, line 21, after "sequence" insert --from the MF$\alpha$1 promoter and MF$\alpha$1 signal sequence--.

Col. 11, line 2, "structual" should be --structural--.

Col. 14, line 4, "FIG." should be --FIGS.--.

Col. 16, line 47, insert under "TCT", --tyr--.

UNITED STATES PATENT AND TRADEMARK OFFICE
CERTIFICATE OF CORRECTION

Page 2 of 2

PATENT NO. : 5,082,783
DATED : January 21, 1992
INVENTOR(S) : Ernst, et. al.

It is certified that error appears in the above-indentified patent and that said Letters Patent is hereby corrected as shown below:

Col. 18, line 21 "RPA" should be --TPA--.

Signed and Sealed this

Thirtieth Day of August, 1994

Attest:

BRUCE LEHMAN

*Attesting Officer*  *Commissioner of Patents and Trademarks*